US010061895B2

(12) United States Patent
Walker

(10) Patent No.: US 10,061,895 B2
(45) Date of Patent: *Aug. 28, 2018

(54) SYSTEM FOR PROVIDING IDENTIFICATION AND INFORMATION, AND FOR SCHEDULING ALERTS

(71) Applicant: SOLOMON SYSTEMS, INC., Springdale, MD (US)

(72) Inventor: Timothy T. Walker, Springdale, MD (US)

(73) Assignee: SOLOMON SYSTEMS, INC., Springdale, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/173,331

(22) Filed: Jun. 3, 2016

(65) Prior Publication Data

US 2017/0024525 A1  Jan. 26, 2017

Related U.S. Application Data

(63) Continuation of application No. 14/856,083, filed on Sep. 16, 2015, now Pat. No. 9,390,231, which is a
(Continued)

(51) Int. Cl.
*G06K 5/00* (2006.01)
*G06F 19/00* (2018.01)
(Continued)

(52) U.S. Cl.
CPC ........... *G06F 19/327* (2013.01); *A61B 90/90* (2016.02); *A61B 90/96* (2016.02); *A61B 90/98* (2016.02);
(Continued)

(58) Field of Classification Search
CPC .......... G06K 5/00; G06K 19/00; G06K 19/06; G06K 7/08; G06K 7/01; G06F 17/00; G06Q 50/00
(Continued)

(56) References Cited

U.S. PATENT DOCUMENTS 5,877,742 A  3/1999  Klink
6,681,003 B2  1/2004  Linder et al.
(Continued)

FOREIGN PATENT DOCUMENTS

JP   7-307803      11/1995
JP   2003067488    3/2003
KR   10-2009-0128962  12/2009

OTHER PUBLICATIONS

Ngail, E., et al., "Design of an RFID-based Healthcare Management System using an Information System Design Theory", Inf Syst Front, 2009, 11:405-417.
(Continued)

*Primary Examiner* — Edwyn Labaze
(74) *Attorney, Agent, or Firm* — Ping Wang; Morris, Manning & Martin, LLP

(57) ABSTRACT

A device and system for providing identification and medical information are disclosed. The device includes a readable code that contains medical biographical information of the subject, a programmable reporter element that is programmed to electronically store at least one particular event relating to the subject, and a signal producing element functionally related to the programmable reporter element. The system includes collecting and storing medical biographical information of a subject, embedding the medical biographical information in a readable code of the device, and scanning the readable code of the device worn by or in the possession of the subject using an appliance to retrieve the medical biographical information of the subject. The
(Continued)

medical biographical information allows medical professionals to obtain the subject's medical information in order to provide medical care. Also disclosed is an integrated system for alerting subjects to upcoming events related to their continued care.

18 Claims, 4 Drawing Sheets

Related U.S. Application Data continuation of application No. 14/458,877, filed on Aug. 13, 2014, now Pat. No. 9,165,335, which is a continuation of application No. 13/917,374, filed on Jun. 13, 2013, now Pat. No. 8,833,649, which is a continuation of application No. 13/313,821, filed on Dec. 7, 2011, now Pat. No. 8,485,439, which is a continuation-in-part of application No. 13/270,672, filed on Oct. 11, 2011, now Pat. No. 8,181,862.

(51) Int. Cl.
| | | |
|---|---|---|
| *G06Q 10/06* | (2012.01) | |
| *G06Q 50/22* | (2018.01) | |
| *G04G 11/00* | (2006.01) | |
| *G04G 13/02* | (2006.01) | |
| *G06K 19/06* | (2006.01) | |
| *G06Q 50/24* | (2012.01) | |
| *A61B 90/96* | (2016.01) | |
| *A61B 90/90* | (2016.01) | |
| *A61B 90/98* | (2016.01) | |
| *G06K 7/14* | (2006.01) | |
| *G16H 40/63* | (2018.01) | |
| *G16H 10/60* | (2018.01) | |
| *G16H 40/20* | (2018.01) | |
| *G16H 50/20* | (2018.01) | |

(52) U.S. Cl.
CPC ............ *G04G 11/00* (2013.01); *G04G 13/02* (2013.01); *G06F 19/3418* (2013.01); *G06K 7/1413* (2013.01); *G06K 19/06046* (2013.01); *G06Q 10/06* (2013.01); *G06Q 50/22* (2013.01); *G06Q 50/24* (2013.01); *G16H 10/60* (2018.01); *G16H 40/20* (2018.01); *G16H 40/63* (2018.01); *G16H 50/20* (2018.01)

(58) Field of Classification Search
USPC .... 235/380, 487, 375, 382.5, 382, 451, 492; 705/3
See application file for complete search history.

(56) References Cited

U.S. PATENT DOCUMENTS

| | | | |
|---|---|---|---|
| 6,751,805 B1 | 6/2004 | Austion | |
| 7,204,808 B1 | 4/2007 | Friedman et al. | |
| 7,434,724 B2 | 10/2008 | Lane | |
| 7,515,053 B2 | 4/2009 | Klein | |
| 7,761,261 B2 | 7/2010 | Shmueli et al. | |
| 8,405,518 B2 | 3/2013 | Corwin et al. | |
| 2001/0045469 A1 | 11/2001 | Hooglander | |
| 2003/0016122 A1 | 1/2003 | Petrick | |
| 2003/0052788 A1 | 3/2003 | Kwong-Tai Chung | |
| 2004/0104271 A1 | 6/2004 | Martucci et al. | |
| 2004/0140898 A1 | 7/2004 | Reeves | |
| 2004/0151071 A1 | 8/2004 | Kocher | |
| 2004/0172283 A1* | 9/2004 | Vanderveen | G06F 19/323 705/2 |
| 2005/0052275 A1 | 3/2005 | Houle | |
| 2007/0074043 A1 | 3/2007 | Lacey | |
| 2007/0156452 A1 | 7/2007 | Batch | |
| 2007/0158411 A1 | 7/2007 | Krieg | |
| 2007/0229287 A1 | 10/2007 | Morgan | |
| 2007/0233520 A1 | 10/2007 | Wehba et al. | |
| 2008/0131362 A1 | 6/2008 | Rousso et al. | |
| 2008/0200774 A1 | 8/2008 | Luo | |
| 2008/0303638 A1 | 12/2008 | Nguyen et al. | |
| 2009/0112770 A1* | 4/2009 | Schmidt | G06Q 50/24 705/51 |
| 2009/0230179 A1 | 9/2009 | Livolsi et al. | |
| 2009/0243833 A1* | 10/2009 | Huang | G06F 19/323 340/505 |
| 2009/0322513 A1 | 12/2009 | Hwang et al. | |
| 2010/0072280 A1 | 3/2010 | McGill et al. | |
| 2010/0088252 A1 | 4/2010 | Le-Henand et al. | |
| 2010/0298899 A1 | 11/2010 | Donnell et al. | |
| 2010/0324936 A1 | 12/2010 | Vishnubhatla et al. | |
| 2011/0001605 A1* | 1/2011 | Kiani | G06F 19/327 340/5.6 |
| 2011/0003610 A1 | 1/2011 | Key et al. | |
| 2011/0057037 A1 | 3/2011 | Frysz et al. | |
| 2011/0092825 A1 | 4/2011 | Gopinathan et al. | |
| 2011/0119080 A1* | 5/2011 | Hayter | A61B 5/14532 705/2 |
| 2011/0127325 A1 | 6/2011 | Hussey et al. | |
| 2011/0153380 A1* | 6/2011 | Velusamy | G06Q 10/109 705/7.19 |
| 2011/0240729 A1 | 10/2011 | Shuck | |
| 2013/0056535 A1 | 3/2013 | Rowlandson et al. | |
| 2013/0262135 A1* | 10/2013 | Nichols | G06Q 50/22 705/2 |
| 2013/0290013 A1 | 10/2013 | Forrester | |
| 2014/0039932 A1 | 2/2014 | Walton, III | |
| 2014/0070012 A1 | 3/2014 | Hunt et al. | |
| 2014/0122118 A1* | 5/2014 | Farr | G06Q 30/0251 705/3 |
| 2014/0263654 A1* | 9/2014 | Davis | G06K 17/0016 235/487 |
| 2015/0163339 A1* | 6/2015 | Fenton | H04M 19/04 455/557 |
| 2015/0213203 A1* | 7/2015 | Cumbie | G06F 19/323 705/3 |
| 2017/0206324 A1* | 7/2017 | Reicher | G06F 19/327 |

OTHER PUBLICATIONS

International Search Report and Written Opinion of the International Searching Authority issued in International Patent Application Serial No. PCT/US2012/052089 dated Jan. 21, 2013.
File history of U.S. Appl. No. 13/313,821, filed Dec. 7, 2011.
File history of U.S. Appl. No. 13/270,672, filed Oct. 11, 2011.
File history of U.S. Appl. No. 13/917,374, filed Jun. 13, 2013.
File history of U.S. Appl. No. 14/458,877, filed Aug. 13, 2014.
File history of U.S. Appl. No. 14/856,083, filed Sep. 16, 2015.

* cited by examiner

SYSTEM FOR PROVIDING IDENTIFICATION AND INFORMATION, AND FOR SCHEDULING ALERTS

This application is a Continuation of U.S. patent application Ser. No. 14/856,083, filed on Sep. 16, 2015, which is a Continuation of U.S. patent application Ser. No. 14/458,877, filed on Aug. 13, 2014, now U.S. Pat. No. 9,165,335, which is a Continuation of U.S. patent application Ser. No. 13/917,374, filed on Jun. 13, 2013, now U.S. Pat. No. 8,833,649, which is a Continuation of U.S. patent application Ser. No. 13/313,821, filed Dec. 7, 2011, now U.S. Pat. No. 8,485,439, which is a Continuation-In-Part of U.S. patent application Ser. No. 13/270,672, filed Oct. 11, 2011, now U.S. Pat. No. 8,181,862. The entirety of the aforementioned applications is incorporated herein by reference.

FIELD

This application generally relates to relates to a system for providing identification and/or information; in particular, medical information. The application further relates to an additional system for alerting a subject to upcoming events.

BACKGROUND

When a subject, to whom lacks the ability to effectively communicate needs urgent medical care, responders typically arrive at the scene within a short period of time without any information regarding the person in distress (i.e., subject). To properly provide medical care, the responders typically ask the subject relevant questions, such as current medications, allergies to medications, prior medical histories, i.e. surgeries, hospital visits, and other conditions. However, even if the subject is alert, he or she typically cannot provide accurate answers to such questions under the circumstances. Consequently, responders often provide urgent medical care without some medical history information. Likewise, after the subject is transported to a medical facility, doctors and other medical personnel at the hospital are not equipped with some of the medical history information regarding the subject, especially if the subject has never gone to the hospital before. Medical personnel may need to contact the subject's physician and/or other hospitals to get the needed information, which can cost time, and potentially life. Therefore, it is a great need for a system which can provide biographical information and allows medical professionals to obtain a subject's medical information.

Additionally, there exists a need for such a system, wherein the system further comprises an integrated element that can remind the subject of upcoming events related to their care and alert practitioners when the subject fails to fulfill those events.

SUMMARY

One aspect of the present application relates to a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element.

Another aspect of the present application relates to a system for providing identification and medical information of a subject in a removable device, comprising: a database for collecting and storing medical biographical information of the subject; a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element; and an appliance for scanning the readable code of the device worn by or in the possession of the subject to retrieve medical biographical information of the subject, wherein the retrieved medical biographical information allows responders to obtain the subject's medical information in order to provide care.

Another aspect of the present application relates to a non-transitory computer readable medium providing instructions for providing identification and medical information, the instructions comprising: collecting and storing medical biographical information of a subject; embedding the medical biographical information in a readable code of a removable device that is adapted to be worn by or in the possession of the subject; scanning the readable code of the device worn by or in the possession of the subject using an appliance to retrieve the medical biographical information of the subject; wherein the medical biographical information allows responders to obtain the subject's medical information in order to provide medical care and wherein the device is not linked to a medical sensor and is worn by the subject in a non-hospital setting; and programming a reporter element that provides a signal to a functionally linked signal producing element to inform the subject of at least one particular event relating to the subject, wherein said programming is by a second system that electronically stores at least one particular event relating to the subject.

BRIEF DESCRIPTION OF THE DRAWINGS

The detailed description will refer to the following drawings, wherein like numerals refer to like elements.

DETAILED DESCRIPTION

Figure 1:
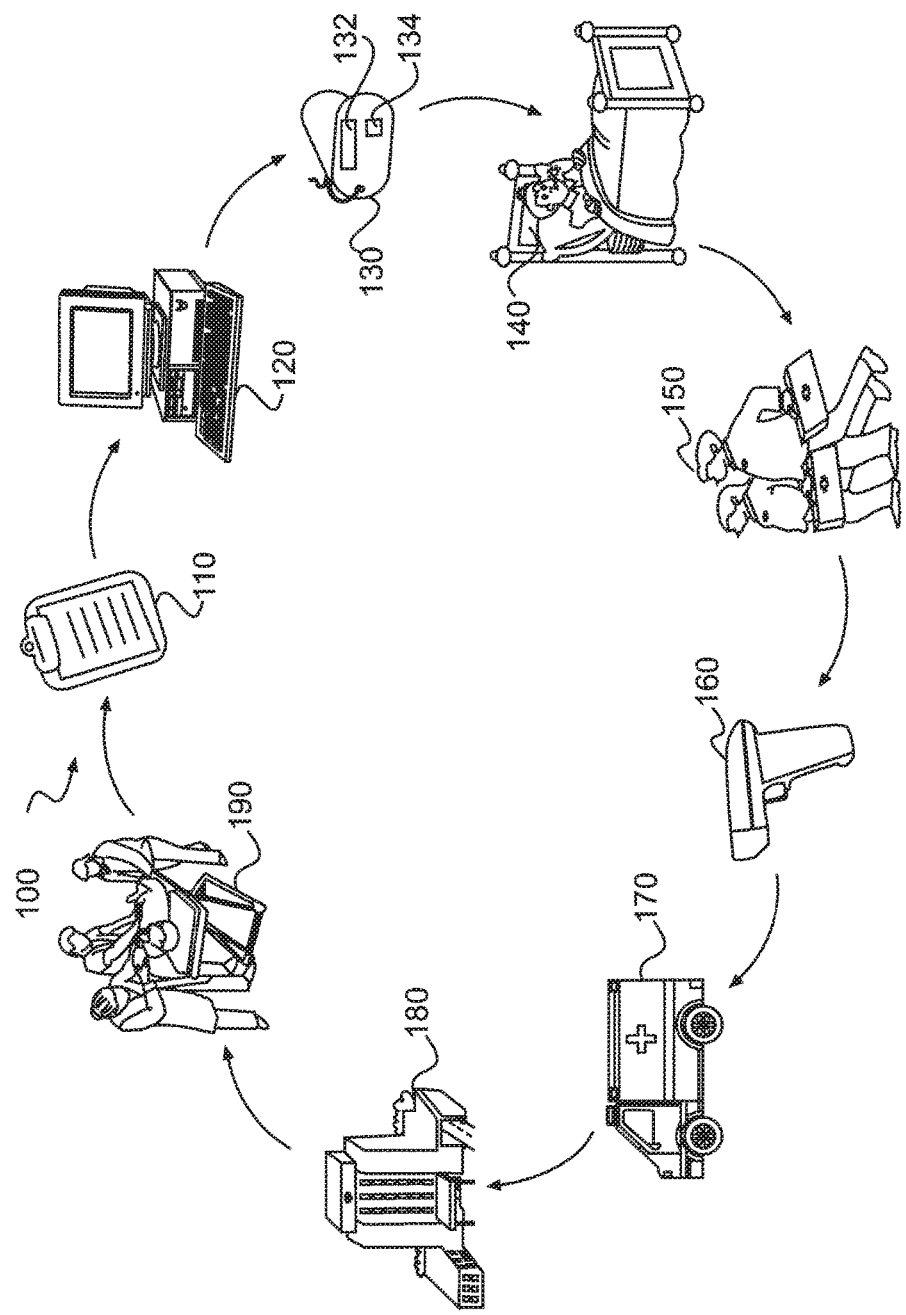
FIG. 1 illustrates an embodiment of the system for providing identification and medical information.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention.

Descriptions of specific applications are provided only as representative examples. The present application is not intended to be limited to the embodiments shown, but is to be accorded the widest possible scope consistent with the principles and features disclosed herein.

One aspect of the present application relates to a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element.

In particular embodiments, the device is not linked to a medical sensor and is worn by the subject in a non-hospital setting.

In particular embodiments, said reporter element is programmed by a second system that electronically stores at least one particular event relating to the subject. In a further embodiment, the second system additionally alerts a medical practitioner if the subject fails to fulfill the event.

In particular embodiments, the event is an appointment. In a further embodiment, said appointment is a medical appointment. In a still further embodiment, said medical appointment is selected from the group consisting of a physical examination, a physical therapy session, a mental examination and a mental therapy session. In another further embodiment, said appointment is a follow-up to a visit by the subject to a medical facility.

In particular embodiments, the reporter element is programmed to issue a signal a predetermined time prior to the at least one particular event. In a further embodiment, the signal repeats or remains until the subject fulfills the event and the reporter element is reset. In a still further embodiment, the reporter element is reset by a medical practitioner.

In particular embodiments, the device further comprises a tracking circuit that is capable of tracking the subject's location.

In particular embodiments, the medical biographical information includes one or more of the subject's name, sex, date of birth, height, weight, blood type, allergies, sicknesses or medical conditions, use of medications, emergency contacts, and complete medical records.

In particular embodiments, the device is a bracelet or a necklace worn by the subject.

Another aspect of the present application relates to a system for providing identification and medical information of a subject in a removable device, comprising: a database for collecting and storing medical biographical information of the subject; a removable device that is adapted to be worn or in the possession of the subject, wherein the device comprises: a readable code that contains medical biographical information of the subject, a programmable reporter element that is programmed to electronically store at least one particular event relating to the subject, and a signal producing element functionally related to the programmable reporter element; and an appliance for scanning the readable code of the device worn by or in the possession of the subject to retrieve medical biographical information of the subject, wherein the retrieved medical biographical information allows responders to obtain the subject's medical information in order to provide care.

In particular embodiments, the system further comprises a computer screen located in an emergency vehicle to display the retrieved medical biographical information.

In particular embodiments, the system further comprises transmitting the retrieved medical biographical information to a medical facility that is designated to receive the subject.

In particular embodiments, the medical biographical information is updated after the subject is treated at the medical facility.

Another aspect of the present application relates to a non-transitory computer readable medium providing instructions for providing identification and medical information, the instructions comprising: collecting and storing medical biographical information of a subject; embedding the medical biographical information in a readable code of a removable device that is adapted to be worn by or in the possession of the subject; scanning the readable code of the device worn by or in the possession of the subject using an appliance to retrieve the medical biographical information of the subject; wherein the medical biographical information allows responders to obtain the subject's medical information in order to provide medical care and wherein the device is not linked to a medical sensor and is worn by the subject in a non-hospital setting; and programming a reporter element that provides a signal to a functionally linked signal producing element to inform the subject of at least one particular event relating to the subject, wherein said programming is by a second system that electronically stores at least one particular event relating to the subject.

In particular embodiments, the computer readable medium further comprises instructions for resetting the reporter element after the subject fulfills the event.

In a particular embodiment, the computer readable medium comprises instructions for displaying the retrieved medical biographical information on a computer screen located in an emergency vehicle when the subject needs medical care.

In another particular embodiment, the computer readable medium comprises instructions for transmitting the retrieved medical biographical information to a medical facility that is designated to receive the subject.

In another particular embodiment, the computer readable medium comprises instructions for tracking the subject's location using a tracking circuit located on the device worn by or in the possession of the subject.

As used herein, a "medical sensor" refers to an appliance or apparatus that measures or monitors a dynamic bodily function, process or condition. Examples of medical sensors are those that measure or monitor heart rate, temperature, blood oxygen or other blood gasses, an electrocardiogram, or an electroencephalogram.

As used herein, a "removable" device refers to an object or device that a subject or a person attending the subject can place on, or remove from, the body, clothing or an accessory (such as a wallet or in a purse or bag) of the subject at will. The removable device is adapted to be worn on a daily basis, at all times, or at only particular times chosen by the subject, such as, but not limited to, during sleep, exercise, at home, travel, work, outdoors, or indoors.

A system and method are disclosed to assist a medical professional or responder to identify and provide appropriate medication and care to subjects unable to communicate for themselves in non-emergency or emergency scenarios.

One aspect of the present application relates to a first system for providing identification and information. In a particular embodiment, as illustrated in FIG. 1, the first system 100 collects a subject's medical biographical information 110 from various sources, such as the subject's doctors' offices, medical facilities that the subject has visited in the past, and medical records or notes prepared or assembled by the subject. Examples of the subject's medical biographical information 110 include name, sex, date of birth, height, weight, blood type, allergies, sicknesses/medical conditions, use of prescribed medications, emergency contacts, as well as complete medical records if available.

In a particular embodiment, the system 100 electronically stores the subject's medical biographical information 110 in a database of a computer system 120. In some embodiments, the subject's medical biographical information 110 stored in the database is updated by the subject's doctors or the subject as needed. The first system 100 embeds the stored subject's medical biographical information 110 in a readable code 132 of a device 130 that is worn by or in the possession of the subject 140. In some embodiments, the device 130 is a bracelet, pendant, key chain, fob, belt clip, dog tag, necklace, jewelry, button or other object that is worn by the subject. In particular embodiments, the device 130 is kept in the subject's wallet, purse or pocket. In particular embodiments, the device is water resistant, water proof or comprises a water proof coating or sheath that protects the readable code. In particular embodiments, the device is wear resistant, wear proof or comprises a wear proof coating or sheath that protects the readable code.

In another embodiment, the device 130 is a card or a computer readable device, such as, but not limited to, a flash drive, solid state storage device, compact disc, or digital video disc (DVD). In particular embodiments, the readable code is contained on the removable device in electronic form.

In other particular embodiments, the readable code is present on the removable device in a printed form. In further embodiments, the printed form may be in the form of a bar code, a binary code, a matrix code, pictogram or a quick response (QR) code.

In some embodiments, the readable code is present on the removable device in both an electronic form and in a printed form. In some further embodiments, the data stored in electronic form and in printed form on the removable device is the same. In other further embodiments, the data stored in electronic form and in printed form on the removable device is different.

In some embodiments, the readable code is. In other embodiments, the readable code is non-encrypted code. In still other embodiments, the readable code is a combination of encrypted code and non-encrypted code.

In particular embodiments, a responder 150 uses an appliance 160 to scan the readable code 132 of the device 130 worn by, or in the possession of, the subject 140. In particular embodiments, the appliance 160 obtains the subject's medical biographical information 110, which may include, for example, the subject's name, sex, date of birth, height, weight, blood type, allergies, medical histories and conditions, sicknesses, use of prescribed medications, emergency contacts, as well as the complete medical records if available.

In particular embodiments, the responder 150 is a paramedic, emergency medical technician (EMT), fire fighter, policeman/woman, medical professional, or care worker. The term "medical professional" or "medical practitioner" as used herein, includes any person who cares for the medical needs of a subject such as, but not limited to, a physician, surgeon, dentist, chiropractor, osteopath, nurse, nurse's aide, orderly or volunteer.

In some embodiments, the appliance 160 is a handheld scanner. In other embodiments, the appliance 160 is a cellular telephone or a computer, including, but not limited to a laptop, pad or tablet computer. In particular embodiments, the appliance 160 includes an integrated display that displays the subject's medical biographical information 110 to assist the responder on the scene to provide care to the subject 140. in another embodiment, the obtained medical biographical information 110 is displayed on a computer or other appliance or equipment. In a particular embodiment, the appliance and/or display is located in an emergency vehicle 170.

In another embodiment, the first system 100 transmits the medical biographical information 110 to a medical facility 180 that is designated to receive the subject 140. The designated medical facility 180 uses the medical biographical information 110 and the current medical needs of the subject 140 to develop a plan for medical care. In a particular embodiment, said plan for medical care is developed before the subject arrives at the designated medical facility 180.

In a particular embodiment, the medical facility 180 is a hospital. In another particular embodiment, the medical facility 180 is an emergency room. In another particular embodiment, the medical facility 180 is an outpatient facility, including an outpatient urgent care facility. In another particular embodiment, the medical facility 180 is a clinic. In another particular embodiment, the medical facility 180 is a nursing home. In another particular embodiment, the medical facility 180 is a physician's office. In yet another particular embodiment, the medical facility 180 is a dentist's office.

In particular embodiments, transmittal of the medical biographical information 110 and the current medical needs of the subject 140 to the medical facility 180 allows a medical professional 190 at the medical facility 180 to be prepared for the subject's 140 arrival.

In particular embodiments, a medical professional 190 and/or responder 150 submits updated medical biographical information 110 to the database 120. In another embodiment, the subject submits updated medical biographical information 110 to the database 120. In particular embodiments, the updated medical biographical information 110 is automatically synced with data embedded in the readable code 132 of the device 130.

In a particular embodiment, the device 130 comprises a GPS or other tracking circuit 134. In particular embodiments, the medical professional 190 tracks the location of the subject 140. In a particular embodiment, the distance and the travel time before arrival at the medical facility 180 is determined.

In particular embodiments, the first system 100 is used for emergency circumstances. In other particular embodiments, the first system 100 is used for non-emergency circumstances. In a related embodiment, the non-emergency circumstance is transport of a subject 140 from one medical facility 180 to a different medical facility 180.

Figure 2:
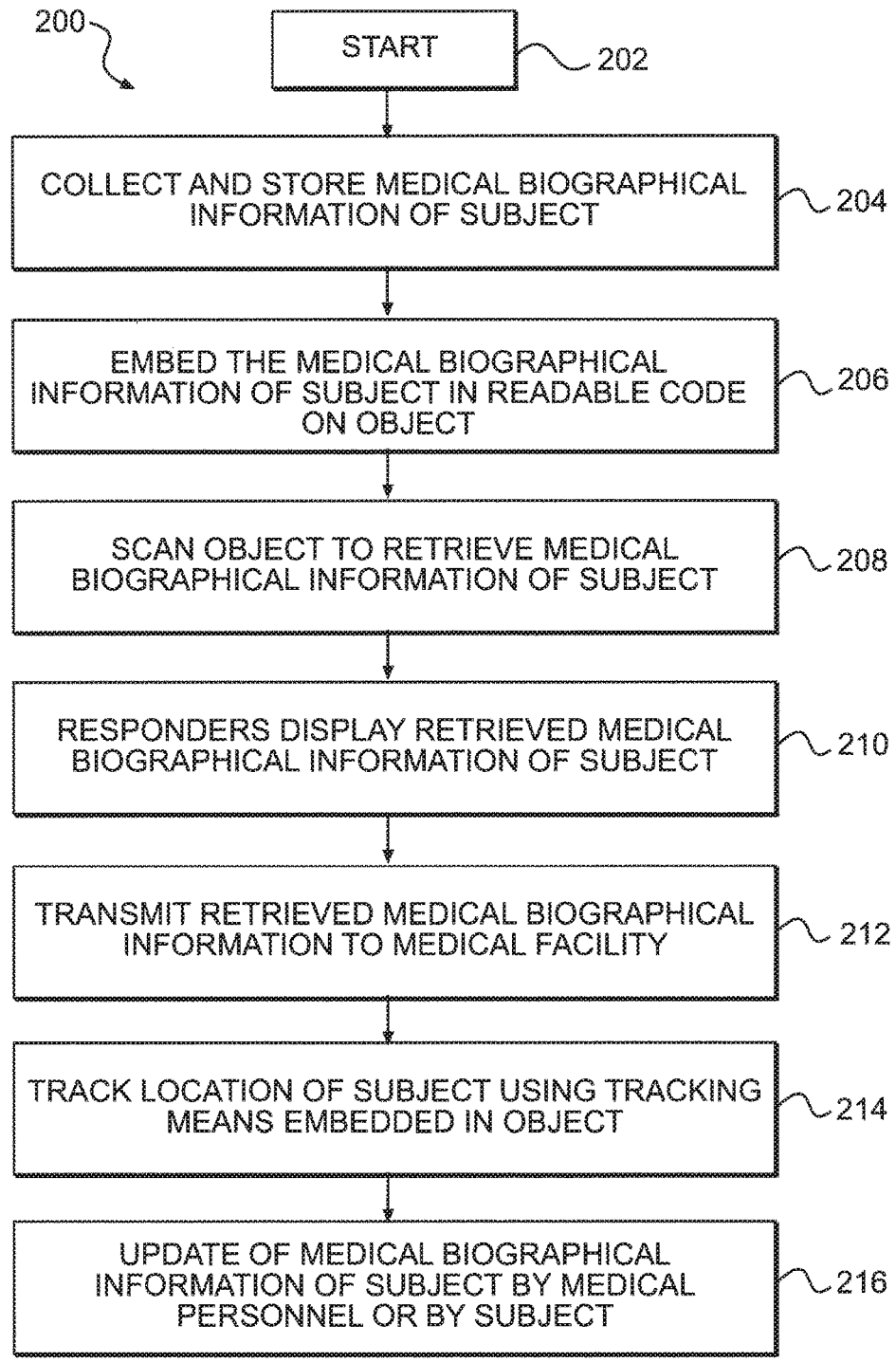
FIG. 2 is a flow charting illustrating an embodiment of the method for providing identification and medical information.

FIG. 2 is a flow chart showing a non-limiting example of an embodiment of a method 200 for providing identification and medical information. In a particular embodiment, method 200 comprises the collection and storage of medical biographical information of the subject 204. In a particular embodiment, the medical biographical information is embedded in a readable code of a device that is adapted to be worn by or in the possession of the subject 206. In particular embodiments, an appliance reads the readable code 208 of the device 206 to retrieve the medical biographical information of the subject 204. In some embodiments, the retrieved medical biographical information 204 is displayed on a computer screen located in an emergency vehicle 210. In particular embodiments, the retrieved medical biographical information 204 is wirelessly transmitted to a medical facility that is designated to receive the subject 212. In some embodiments, the location of the subject is determined using a GPS tracking circuit located on the device worn by the subject 214. In particular embodiments, the medical biographical information 204 is updated by a medical professional or responder 216.

Figure 3:
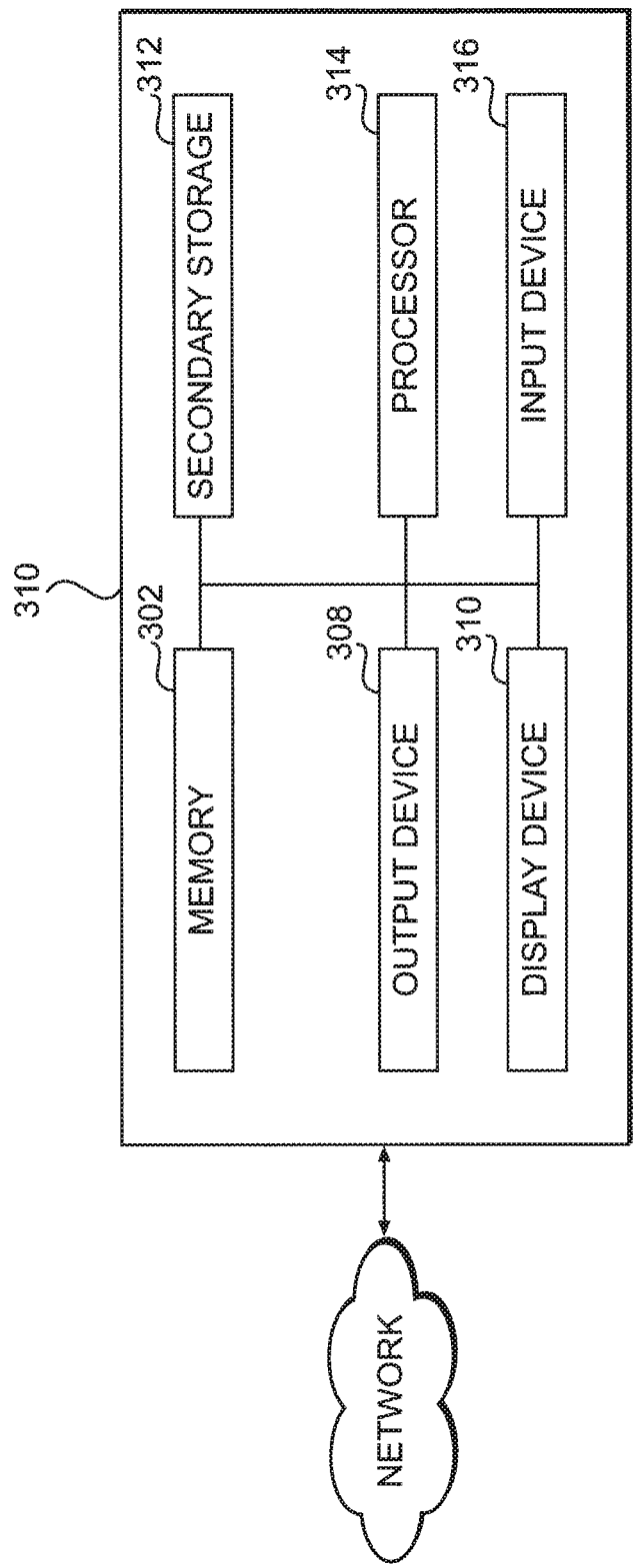
FIG. 3 is a block diagram illustrating exemplary hardware components of the exemplary computer system or server for implementing embodiments of the system and method for providing identification and medical information.

In particular embodiments, as illustrated in FIG. 3, the system disclosed in the present application comprises a computer system or server 300 for implementing embodiments of the system 100 (FIG. 1) and method 200 (FIG. 2) for providing identification and medical information. In an exemplary embodiment, the computer system or server 300 is the computer system 120 of FIG. 1. In particular embodiments, the computer system or server 300 includes and executes software programs to perform functions described herein, including the steps of the method 200 described above. In other embodiments, computer system 300 is a mobile device that performs the steps of the method 200 described above. In particular embodiments. The computer system 300 connects with a network 318, to receive inquires, obtain data, and transmit information as described above. In some embodiments, the network is the internet. In other embodiments, the network is an intranet, WAN, or LAN.

In an exemplary embodiment, the computer system 300 includes a memory 302, a processor 314, and, optionally, a secondary storage device 312. In some embodiments, the computer system 300 includes a plurality of processors 314 and is configured as a plurality of, e.g., bladed servers, or other known server configurations. In particular embodiments, the computer system 300 also includes an input device 316, a display device 310, and an output device 308. In some embodiments, the memory 302 includes RAM or similar types of memory. In particular embodiments, the memory 302 stores one or more applications for execution by the processor 314. In some embodiments, the secondary storage device 312 includes a hard disk drive, floppy disk drive, CD-ROM or DVD drive, or other types of non-volatile data storage. In particular embodiments, the processor 314 executes the application(s) that are stored in the memory 302 or the secondary storage 312, or received from the internet or other network 318. in some embodiments, processing by the processor 314 may be implemented in software, such as software modules, for execution by computers or other machines. These applications preferably include instructions executable to perform the functions and methods described above and illustrated in the Figures herein. The applications preferably provide GUIs through which users may view and interact with the application(s).

In some embodiments, the processor 314 may execute one or more software applications in order to provide the functions described in this specification, specifically to execute and perform the steps and functions in the methods described above. Such methods and the processing may be implemented in software, such as software modules, for execution by computers or other machines. The GUIs may be formatted, for example, as web pages in HyperText Markup Language (HTML), Extensible Markup Language (XML) or in any other suitable form for presentation on a display device depending upon applications used by users to interact with the system 100.

In particular embodiments, the input device 316 may include any device for entering information into the computer system 300, such as a touch-screen, keyboard, mouse, cursor-control device, microphone, digital camera, video recorder or camcorder. The input device 316 may be used to enter information into GUIs during performance of the methods described above. In some embodiments, the display device 310 may include any type of device for presenting visual information such as, for example, a computer monitor or flat-screen display, mobile device screen, or a printer. The display device 310 may display the GUIs and/or output from a software program. In particular embodiments, the output device 308 may include any type of device for presenting a hard copy of information, such as a printer, and other types of output devices include speakers or any device for providing information in audio form.

Exemplary embodiments of the computer system 300 include dedicated server computers, such as bladed servers, personal computers, laptop computers, notebook computers, palm top computers, network computers, mobile devices, or any processor-controlled device capable of executing a web browser or other type of application for interacting with the system.

In particular embodiments, the first system 100 and/or method 200 may use multiple computer systems or servers as necessary or desired to support the users and may also use back-up or redundant servers to prevent network downtime in the event of a failure of a particular server. In addition, although aspects of an implementation consistent with the above are described as being stored in the memory 302, one skilled in the art will appreciate that these aspects can also be stored on or read from other types of computer program products or computer-readable media, such as secondary storage devices 312, including hard disks, floppy disks, or CD-ROM; DVD or other forms of RAM or ROM. In particular embodiments, the computer-readable media may include instructions for controlling a computer system, such as the computer system 300, to perform a particular method, such as the methods described above.

Figure 4:
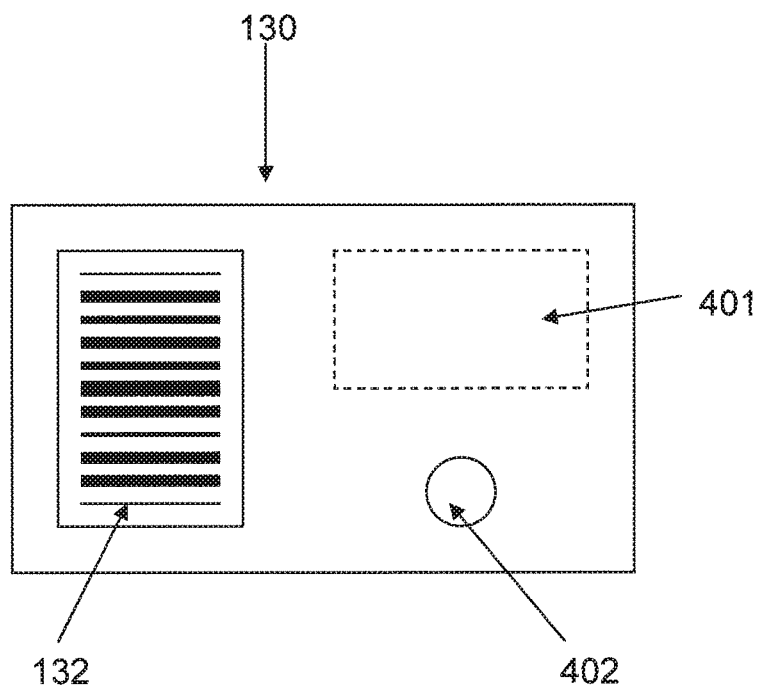
FIG. 4 is a representative schematic view of the elements of the removable device.

One aspect of the present application relates to a removable device that is adapted to be worn or in the possession of the subject, as exemplified in the non-limiting example shown in FIG. 4. The device 130 comprises a readable code 132 that contains medical biographical information of the subject, a programmable reporter 401 that electronically stores at least one particular event relating to the subject, and a signal producing element 402 functionally related to the programmable reporter element.

In a particular embodiment, the removable device 130 that is adapted to be worn or in the possession of the subject consists of a readable code 132 that contains medical biographical information of the subject, a programmable reporter element that is programmed by a second system that electronically stores at least one particular event relating to the subject, and a signal producing element functionally related to the programmable reporter element.

In a particular embodiment, the reporter element 401 is programmed to store data regarding at least one particular event relating to the subject and an algorithm for producing an alert signal in the signal producing element 402 to inform the subject of the at least one particular event relating to the subject. In a further embodiment, the alert signal is a light signal. In another embodiment, the signal is an audible signal. In yet another embodiment, the alert signal is a vibrating signal. In yet another embodiment, the alert signal is an alphanumeric display on a LED or LCD display. In yet another embodiment, the alert signal is a signal transmitted from the device to a caregiver or medical practitioner. In yet another embodiment, the device comprises two or more alert signals that are functionally related to the programmable reporter element, comprising two or more of the same type of alert signal or any combination thereof. In a particular embodiment, the reporter element is a separate element of the removable device 130 from the readable code 132.

In particular embodiments, at least one signal producing element of the device is a transmitter. In a related embodiment, the reporter element signals notification of an upcoming event and/or an unfulfilled event related to the subject to a family member, friend, caregiver and/or medical practitioner.

In a particular embodiment, the removable device further comprises a power source for the reporter element and the signal producing element. In a further embodiment, the power source is a battery. In a still further embodiment, the battery is rechargeable. In another still further embodiment, the battery is removable. In another further embodiment, the removable device further comprises a solar cell for recharging the power source.

In a particular embodiment, the removable device that is adapted to be worn or in the possession of the subject consists of a readable code that contains medical biographical information of the subject, a programmable reporter element that is programmed by a second system that electronically stores at least one particular event relating to the subject, a signal producing element functionally related to the programmable reporter element, and a power source.

Another aspect of the present application relates to a system for providing identification and medical information of a subject in a removable device, comprising: a database for collecting and storing medical biographical information of the subject; a removable device that is adapted to be worn by or in the possession of the subject, the device including a readable code that contains medical biographical information; and an appliance for scanning the readable code of the device worn by or in the possession of the subject to retrieve the medical biographical information of the subject, wherein the medical biographical information allows responders to obtain the subject's medical information in order to provide care and wherein the device is not linked to a medical sensor and is worn by the subject in a non-hospital setting, and wherein the device worn by or in the possession of the subject further comprises a reporter element that provides a signal to inform the subject of at least one particular event relating to the subject.

In a particular embodiment, said reporter element is programmed manually.

In another particular embodiment, said reporter element is programmed by a second system that electronically stores at least one particular event relating to the subject. In a further particular embodiment, the second system is the same as the first system. In another further particular embodiment, the second system is separate from the first system.

In a particular embodiment, the at least one particular event is an appointment. In some embodiments, the appointment is a follow-up to a visit by the subject to a medical facility. In a further embodiment, the appointment is a medical appointment. In some embodiments, the medical appointment is selected from the group consisting of a physical examination, a physical therapy session, a mental examination and a mental therapy session. In another particular embodiment, the event is a reminder to schedule an appointment.

In a particular embodiment, the reporter element is programmed to issue a signal a predetermined time prior to the event. In a related embodiment, the predetermined time is about one month prior to the event. In another related embodiment, the predetermined time is about two weeks prior to the event. In another related embodiment, the predetermined time is about one week prior to the event. In other related embodiments, the predetermined time is about 30, 28, 25, 21, 20, 15, 14, 7, 6, 5, 4, 3, 2 or 1 day(s) prior to the event. In another related embodiment, the predetermined time is about 24, 18, 12, 6, 5, 4, 3, 2, or 1 hour(s) prior to the event.

In a particular embodiment, the signal repeats or remains until the subject fulfills the event and the reporter element is reset. In a particular embodiment, the reporter element is reset by the subject. In another particular embodiment, the reporter element is reset by a relative, friend or caregiver. In another particular embodiment, the reporter element is reset by a medical practitioner. In a particular embodiment, the reporter element is reset manually. In another particular embodiment, the reporter element is reset by resetting the second system.

In another particular embodiment, the reporter element is programmed to issue an alert signal a predetermined time after the event if the event was not fulfilled or the reporter element was not reset. In a related embodiment, the warning signal is issued on a repeating basis. In a related embodiment, the predetermined time is 15, 30, 45 or 60 minutes after the scheduled time of the event. In another related embodiment, the predetermined time is 1, 2, 3, 4, 5, 6, 12, 18 or 24 hour(s) after the scheduled time of the event. In another related embodiment, the predetermined time is 1, 2, 3, 4, 5, 6, 7, 14, 15, 20, 21, 25, 28 or 30 day(s) after the scheduled time of the event.

In some embodiments, the reporter element is programmed to issue an alert signal before an event in addition to, if the event is not fulfilled by the subject, after said event. In particular embodiments, the signals before and after the event are the same. In other particular embodiments, the signals before and after the event are different.

In a particular embodiment, if the subject fails to fulfill the event, the second system alerts a medical practitioner.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A removable device that is adapted to be worn or in the possession of the subject, wherein the device comprises:
   a readable code that contains medical biographical information of the subject,
   a programmable reporter element that is programmed to electronically store information relating to a scheduled medical appointment by the subject, and
   a signal producing element functionally related to the programmable reporter element, wherein the reporter element is programmed to issue an alert signal before the medical appointment and issue an alert signal when the medical appointment is not fulfilled by the subject.

2. The removable device of claim 1, wherein the device is not linked to a medical sensor and is worn by the subject in a non-hospital setting.

3. The device of claim 1, wherein said reporter element is programmed by a second system that electronically stores information relating to the medical appointment.

4. The system of claim 3, wherein the second system additionally alerts a medical practitioner if the subject fails to fulfill the medical appointment.

5. The device of claim 1, wherein said medical appointment is selected from the group consisting of a physical examination, a physical therapy session, a mental examination and a mental therapy session.

6. The device of claim 1, wherein said medical appointment is a follow-up to a visit by the subject to a medical facility.

7. The device of claim 1, wherein the reporter element is programmed to issue a signal a predetermined time prior to the medical appointment.

8. The device of claim 1, wherein the signals before and after the medical appointment are the same.

9. The device of claim 1, wherein the signals before and after the medical appointment are different.

10. The device of claim 1, further comprising a tracking circuit that is capable of tracking the subject's location.

11. The device of claim 1, wherein the medical biographical information includes one or more of the subject's name, sex, date of birth, height, weight, blood type, allergies, sicknesses or medical conditions, use of medications, emergency contacts, and complete medical records.

12. The device of claim 1, wherein the device is a bracelet or a necklace worn by the subject.

13. A system for providing identification and medical information of a subject in a removable device, comprising:
a database for collecting and storing medical biographical information of the subject;
the removable device of claim 1; and
an appliance for scanning the readable code of the device worn by or in the possession of the subject to retrieve medical biographical information of the subject,
wherein the retrieved medical biographical information allows responders to obtain the subject's medical information in order to provide care.

14. The system of claim 13, further comprising a computer screen located in an emergency vehicle to display the retrieved medical biographical information.

15. The system of claim 13, further comprising transmitting the retrieved medical biographical information to a medical facility that is designated to receive the subject.

16. The system of claim 13, wherein the medical biographical information is updated after the subject is treated at the medical facility.

17. A method for providing identification and medical information of a subject in a removable device, comprising:
collecting and storing medical biographical information of a subject;
embedding the medical biographical information in a readable code of a removable device that is adapted to be worn by or in the possession of the subject;
scanning the readable code of the device worn by or in the possession of the subject using an appliance to retrieve the medical biographical information of the subject; and
transmitting the retrieved medical biographical information to a medical facility,
wherein the subject is admitted to the medical facility for treatment following receipt of the medical biographical information.

18. A method for issuing a medical alert to a removable device adapted to be worn or in the possession of a subject, comprising:
collecting and storing medical biographical information of a subject in the removable device, wherein the medical biographical information comprises information about a scheduled medical appointment;
embedding the medical biographical information in a readable code of the removable device;
scanning the readable code of the device using an appliance to retrieve the medical biographical information of the subject; and
transmitting the retrieved medical biographical info' nation to a medical facility,
wherein the removable device is programmed to issue an alert signal before the medical appointment and issue an alert signal when the medical appointment is not fulfilled by the subject.

* * * * *